United States Patent [19]

Mikasa et al.

[11] 4,305,906
[45] Dec. 15, 1981

[54] APPARATUS FOR ANALYZING OXYGEN, NITROGEN AND HYDROGEN CONTAINED IN METALS

[75] Inventors: Hajime Mikasa; Katsuya Tsuji; Hirofumi Ono, all of Kyoto, Japan

[73] Assignee: Horiba, Ltd., Kyota, Japan

[21] Appl. No.: 164,015

[22] Filed: Jun. 30, 1980

[30] Foreign Application Priority Data

Aug. 15, 1979 [JP] Japan .................................. 54-104319

[51] Int. Cl.$^3$ ...................... G01N 21/00; G01N 31/06; G01N 31/08; G01N 7/00
[52] U.S. Cl. ........................................ 422/62; 422/69; 422/89; 73/19; 73/23.1; 23/232 C
[58] Field of Search ....................... 23/232 C, 230 PC; 422/62, 68, 69, 78, 80, 89, 90, 93, 94, 95; 73/19, 23.1, 27 R

[56] References Cited

U.S. PATENT DOCUMENTS 3,285,701 11/1966 Robertson .......................... 23/232 C
3,949,590 4/1976 Boillot ..................................... 73/19
4,098,576 7/1978 Judge ................................... 422/68

OTHER PUBLICATIONS

Gas Chromatography Abstracts 1967, 135, p. 25.
Heftman; Erich, *Chromatography*, Van Nostrand Reinhold Co., 3rd Edition, 1975, pp. 883-887.

*Primary Examiner*—William F. Smith
*Assistant Examiner*—Chris Konkol
*Attorney, Agent, or Firm*—Wenderoth, Lind & Ponack

[57] ABSTRACT

An apparatus for analyzing oxygen, nitrogen and hydrogen which are contained in metals. The apparatus includes a graphite crucible which has a sample therein and which is heated to generate a gaseous mixture of CO, $N_2$ and $H_2$. An oxidizer is used to oxidize the CO and $H_2$ into $CO_2$ and $H_2O$, respectively. The apparatus further includes a thermal conductivity detecting means for detecting $CO_2$, $N_2$ and $H_2O$, coming from a first gas-chromatographic column which is used for separating $H_2O$ from the $CO_2$ and $N_2$. A second gas-chromatographic column is used for separating $CO_2$ from $N_2$. A passage change valve is used for back-flushing the first column. Helium is preferably used as the carrier gas. The apparatus is simple and operates quickly because the three components, O, N and H, can be measured by using a single carrier gas He and a single sample and thus, only a single measurement operation is required.

5 Claims, 4 Drawing Figures

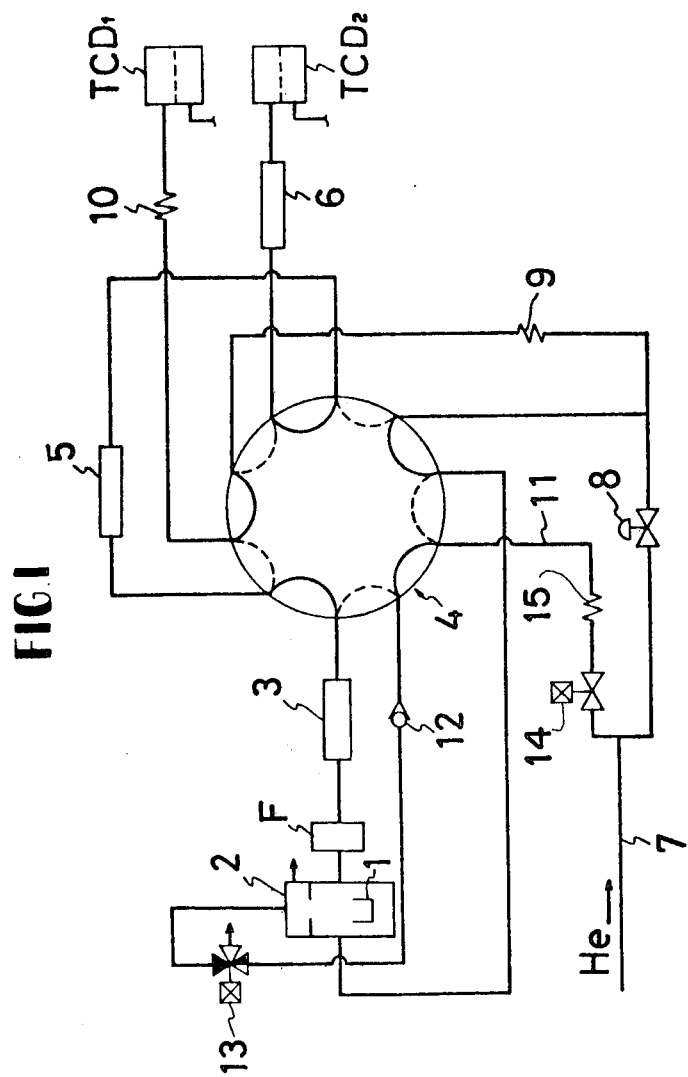

APPARATUS FOR ANALYZING OXYGEN, NITROGEN AND HYDROGEN CONTAINED IN METALS

BACKGROUND OF THE INVENTION

1. Field of the Invention

The present invention relates to an apparatus for analyzing gases such as oxygen (hereinafter referred to as "O"), nitrogen (hereinafter referred to as "N") and hydrogen (hereinafter referred to as "H") which are contained in metals.

2. Description of the Prior Art

The analysis of O, N and H contained in metals has conventionally been done by treating gaseous components such as carbon monoxide (CO), gaseous nitrogen ($N_2$) and gaseous hydrogen ($H_2$), which are generated from O, N and H which are respectively contained in a sample being analyzed, by heating the sample to about 3,000° C. in a graphite crucible with inert gases which are contained therein and which serve as carrier gases. The gaseous components are then detected by means of a Thermal Conductivity Detector (TCD). However, this method involves and requires a two-stage measurement Specifically, the measurement of O and N is performed first and then, the measurement of H is performed. Helium (He) has been used as the carrier gas in the measurement of O and N, while argon (Ar) has been used as the carrier gas in the measurement of H. Such required two-stage measurement has been mentioned due to the fact that He is similar to $H_2$ and Ar is similar to $CO_2$, as well as to $N_2$, with respect to their respective thermal conductivities at the same temperature when a Thermal Conductivity Detector (TCD) is used.

In practice, the measurement of O as well as N and H has been done as follows:

(I) The measurement of O and N

He is used as the carrier gas.

Co, $N_2$ and $H_2$ are generated by heating the sample at a high temperature in a graphite crucible. Subsequently, $H_2$ and CO are oxidized to form water vapor ($H_2O$) and carbon dioxide ($CO_2$), respectively, by bringing them into contact with an oxidizing agent such as cupric oxide which is heated to a temperature of approximately 400° C. The $H_2O$ thus obtained is removed by a dehydrator such as magnesium perchlorate and the $N_2$ and $CO_2$ are separated out by passing the mixed gases through a gas-chromatographic column (Silica gel or the like is used) and then the $N_2$ and $CO_2$ are detected by the TCD. Since it is difficult to quickly and completely separate the three components (CO, $N_2$ and $H_2$) by means of a gas-chromatographic column, an oxidizing agent is used. Further, since the $H_2O$ causes deterioration of the gas-chromatographic column for separating $N_2$ from $CO_2$, a dehydrator is used.

(II) The measurement of H

Ar is used as the carrier gas.

CO, $N_2$ and $H_2$ are generated in the same way as in (I). Subsequently, CO is oxidized into $CO_2$ by bringing the gaseous mixture, which is obtained, into contact with a normal temperature oxidizing agent such as sodium periodate which does not oxidize $H_2$ but oxidizes CO. The $CO_2$ thus obtained is removed by an absorber such as soda-asbestos and the mixture of $N_2$ and $H_2$ is introduced into a gas-chromatographic column to thereby separate $N_2$ from $H_2$. The $H_2$ is then detected by the TCD. Since the $CO_2$ causes deterioration of the gas-chromatographic column for separating $N_2$ and $H_2$, it is removed by an absorber.

As described above, separate samples are required for the measurement of O and N, and for the measurement H, when measuring O, N and H which is contained in metals. More particularly, in the above-described apparatus, it is necessary to use carrier gases, agents, gas-chromatographic columns or the like, all of which are determined in accordance with what is being analyzed. Another requirement is that the preliminary operations such as baking of the empty graphite crucible, and purging of the system have to be repeated and, as a result, the measurement is delayed. In addition to the above described disadvantages, the conventional method has included additional problems with respect to the complicated nature of the apparatus, and results in increased costs or the like.

In view of the large number of problems found in the prior art, the present invention is directed to solving some of those problems. Specifically, it was found that the thermal conductivity of $H_2O$ is similar to that of $CO_2$ and $N_2$ and that a sharp peak can be obtained for the $H_2O$ by back-flushing a gas-chromatographic column for separating $H_2O$ from $N_2$, as well as $CO_2$, even though the elution time for the $H_2$ is longer than that for $N_2$ and $CO_2$. There has been developed an apparatus for analyzing the three components (O, N, H), which are contained in a single sample, which requires only one measurement operation, with He being used as the only carrier gas.

SUMMARY OF THE INVENTION

It is therefore an object of the present invention to provide a gaseous component analyzing apparatus which can easily and speedily measure three components such as O, N and H which are contained in metals.

The object of the invention can be attained by providing an analyzing apparatus which includes a graphite crucible for receiving a sample, a heating furnace for heating the crucible to generate a gaseous mixture of CO, $N_2$ and $H_2$, an oxidizing device for oxidizing CO and $H_2$ contained in a gaseous mixture of CO, $N_2$ and $H_2$ which is into $CO_2$ and $H_2O$, respectively, and a thermal conductivity detector, or a plurality of detectors, for detecting $CO_2$, $N_2$, and $H_2O$. A first gas-chromatographic column is used for separating $H_2O$ from $CO_2$ and $N_2$. A second gas-chromatographic column is used for separating $CO_2$ and $N_2$ and a passage change valve which is used for back-flushing the first gas-chromatographic column is provided so that O, N, H which are contained in said sample can be measured with He being used as the carrier gas.

The apparatus according to the present invention can measure the three components O, N and H through a single measurement operation and by using a single carrier gas (He) and a single sample. A result is that the measurement operation is fast and the construction of the apparatus is very simple.

The elimination of the use of a dehydrator, absorber for $CO_2$ or the like, results in a reduction of dead-space or unused space in the passages of the apparatus, an improvement in maintenance, a prevention of deterioration of the second gas-chromatographic column over a long term due to the fact that $H_2O$ does not enter into the second gas-chromatographic column.

BRIEF DESCRIPTION OF THE DRAWINGS

The present invention will now be described in detail with reference to the accompanying drawings, in which:

FIG. 1 is a schematic diagram of one embodiment of the apparatus of the present invention.

DETAILED DESCRIPTION OF THE INVENTION

Figure 2A:
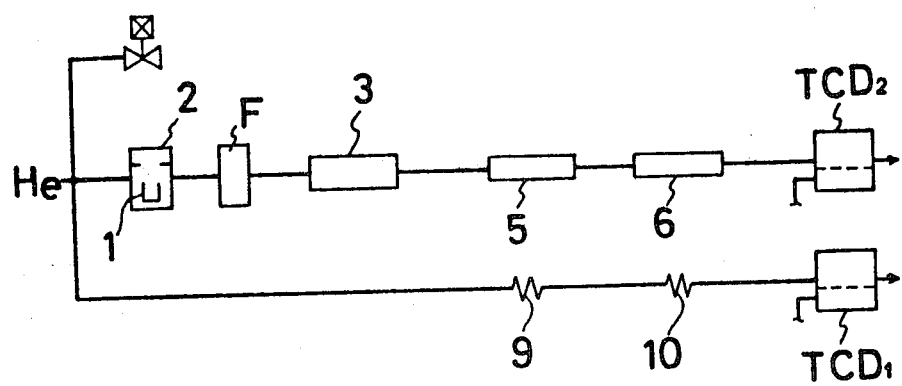
FIG. 2 (A) and FIG. 2 (B) are flow diagrams showing different direction of flow circuits for the apparatus of FIG. 1, FIG. 2 (A) showing a circuit when a passage change valve is in the position shown by the solid lines in FIG. 1, and FIG. 2 (B) showing a circuit when the valve is in the position shown by the dashed lines in FIG. 1.

Various embodiments of the present invention will now be explained in connection with the accompanying drawings.

FIG. 1 shows an example of the analyzing apparatus of the present invention. A graphite crucible 1, which receives a sample therein, is operatively connected to and positioned within a heating furnace 2 for extracting gases from the sample. A filter F connected to the interior of the furnace and an oxidizing device 3 connected on the other side of the filter F. The oxidizing device 3 contains an oxidizing agent, such as cupric oxide, therein.

There is a passage change valve 4, which is used for back flushing, and which is operatively connected in line with the above-described elements. Further, there is a first gas-chromatographic column 5, connected to the valve 4, which is used for separating $H_2O$ from $CO_2$ and $N_2$. Still further, there is a porous polymeric filler contained in the column 5 which has a longer elution time for $H_2O$ than for $CO_2$ and $N_2$. A second gas-chromatographic column 6 is also connected to the passage change valve 4 and is used for separating $CO_2$ from $N_2$. Further, the filler contained in the second column 6 is a silica gel.

A thermal conductivity detector $TCD_1$ which is used for detecting $H_2O$ is connected to valve 4. Likewise, a second thermal conductivity detector $TCD_2$ which is connected to the output of column 6, is used for detecting $CO_2$ and $N_2$ and is also connected to the valve 4. A carrier gas supply conduit 7 (He is the gas used) serves to supply a carrier gas through a pressure regulator 8.

Pneumatic resistances 9 and 10 which are, for example, capillary tubes, provide resistances which are generally substantially equal to that of the first gas-chromatographic column 5 and the second gas-chromatographic column 6, respectively. More particularly, the resistance 9 is equal to the resistance of column 5, and the resistance 10 is equal to the resistance of column 6. However, pneumatic resistance 10 is such that it can be reduced to increase a flux which is generated in the backflushing line so as to promote back-flushing of $H_2O$.

A purging channel 11, of the heating furnace 2, branches out from the gas supply conduit 7. The purging channel 11 has a check valve 12, a three-way valve 13, an electromagnetic valve 14 and a pneumatic resistance 15 disposed therein for controlling flow therethrough.

Figure 2B:
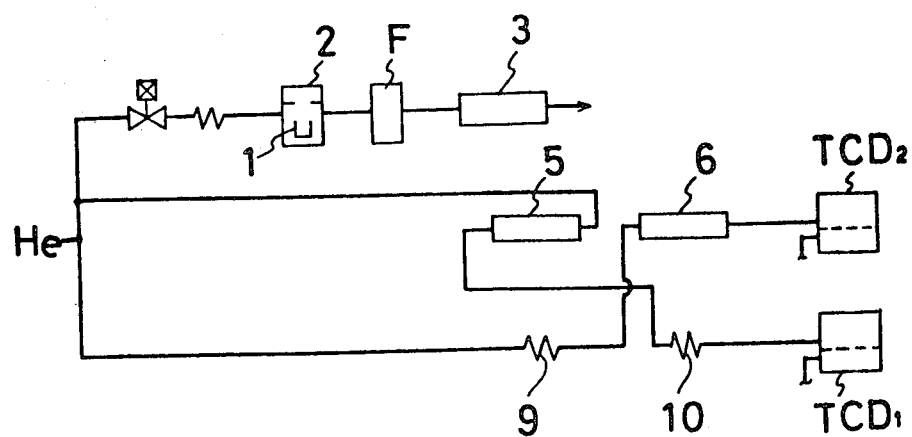

The parts of the apparatus having been described, the method of analyzing by means of said apparatus shall now be described in detail. FIG. 2 (A) and FIG. 2 (B) show the connnection of passages in the situation when the passage change valve 4 is changed over to the condition shown by the solid lines and the condition shown by the dashed lines of FIG. 1, respectively.

Initially, the graphite crucible 1 is placed in the heating furnace 2 and the heating furnace 2 is then energized to heat said graphite crucible 1 while the apparatus is in the condition shown by the dashed lines of FIG. 1 (heating while empty).

The sample is then placed in the graphite crucible 1 and the passages are returned to the condition shown by the solid lines of FIG. 1, which at this time, is the standby condition. In such a condition, the graphite crucible 1 is at room temperature.

Subsequently, the heating furnace is energized to heat said graphite crucible rapidly to about 3,000° C. O, N and H, which are contained in the sample, are subjected to thermal decomposition and CO, $N_2$ and $H_2$ are generated.

In FIG. 2 (A), the gases are shown being transferred into the oxidizer 3 by the carrier gas He. The CO and $H_2$, in the oxidizer 3, are transformed into $CO_2$ and $H_2O$, respectively. The gaseous mixture thus obtained and consisting of $CO_2$, $N_2$ and $H_2O$, is introduced into the first gas-chromatographic column 5. $N_2$ and $CO_2$ are then separated from the $H_2O$ in the first gas-chromatographic column.

The passages are then changed over to the condition shown by the dashed lines of FIG. 1, by means of the passage change valve 4, at the time when the $N_2$ and $CO_2$ have finished eluting through the gas-chromatographic column 5. $H_2O$ remaining in the first gas-chromatographic column 5 is back-flushed and the peak of $H_2O$, which is eluted in the opposite direction, is detected by $TCD_1$ (see FIG. 2 (B). As described above, the sensitivity is not high enough when $H_2$ is detected by $TCD_1$ with He being used as the carrier gas. However, the sensitivity is sufficiently high when $H_2$ is transformed into $H_2O$ and the thus obtained $H_2O$ is detected by $TCD_1$. The sensitivity in this case is similarly high for the measurement of $N_2$ and $CO_2$. Although it is difficult to measure all of the $N_2$, $CO_2$ and $H_2O$ by means of a single column because the adsorption of the $H_2O$ is great, the sharp peak of $H_2O$ can be obtained by using both the first column for separating $H_2O$ from $N_2$ and $CO_2$ and the second column for separating $N_2$ from $CO_2$ and by back-flushing the first column.

Likewise, simultaneously with the detection of $H_2O$, the gaseous mixture of $N_2$ and $CO_2$, which is eluted from the first column 5, is introduced into the second column 6 wherein $N_2$ is separated from $CO_2$ and each peak is detected by $TCD_2$.

Thus, the three components O, N and H, which are contained in the single sample, can be simultaneously measured by only one measuring operation, with He being used as thecarrier gas.

Figure 3:
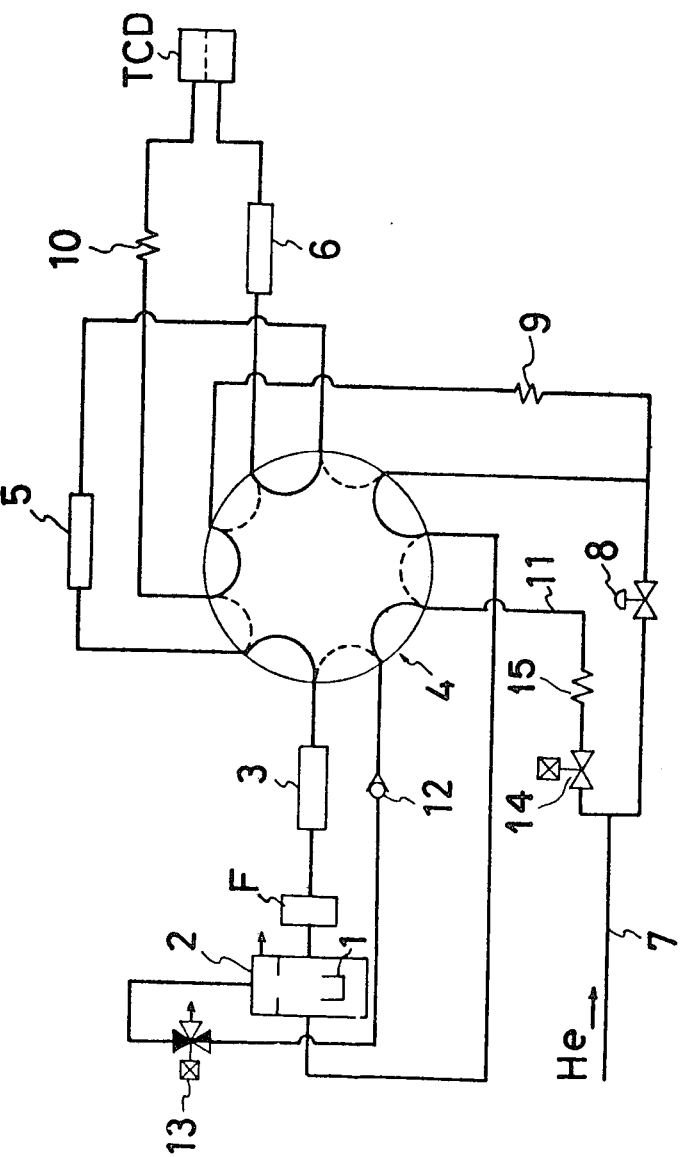
FIG. 3 is a diagram similar to FIG. 1, but of another embodiment of the present invention.

As shown in FIG. 2 (B), when back-flushing is carried out when the passages are changed over to the condition shown by the dashed lines in FIG. 1, the operator can purge the device and prepare for the next measurement by passing the carrier gas (He) in order, through the heating furnace 2, the filter F, the oxidizer 3 and then to the atmosphere. FIG. 1 and FIGS. 2 (A) and (B) illustrate an embodiment having two columns 5 and 6, double passages and two detectors $TCD_1$ and TCD$_2$. However, the measurement can be done by means of only one detector TCD as shown in FIG. 3. In the embodiment shown in FIG. 3, CO$_2$ and N$_2$ are detected by means of the detector TCD first, (at this time H$_2$O remains in said first column 5) and then H$_2$O remaining in the first column 5 is back-flushed. Furthermore, if H$_2$O is back-flushed at the time when the CO$_2$ and N$_2$ are finished eluting from the first column 5, it is necessary to prevent CO$_2$, N$_2$ and H$_2$O from simultaneously arriving at the TCD. This is done by lengthening the second column 6 to delay the elution CO$_2$ and N$_2$.

What is claimed is:

1. An apparatus for analyzing respective quantities of oxygen, nitrogen and hydrogen contained in metals, said apparatus comprising:
   a graphite crucible for receiving a metal sample therein;
   a heating furnace operatively associated with said crucible for heating said crucible and sample and thereby generating a gaseous mixture of CO, N$_2$ and H$_2$;
   supply means for supplying a carrier gas for carrying away said gaseous mixture of CO, N$_2$ and H$_2$;
   oxidizing means connected to said heating furnace for receiving said gaseous mixture and oxidizing said gaseous mixture into a mixture of H$_2$O, CO$_2$ and N$_2$;
   a first gas-chromatographic column for separating the H$_2$O from said mixture;
   a second gas-chromatographic column for separating the N$_2$ from the CO$_2$;
   first thermal conductivity detecting means for detecting quantities of H$_2$O generated from sid sample;
   second thermal conductivity detecting means connected to said second gas-chromatographic column for detecting quantities of CO$_2$ and N$_2$ generated from said sample; and
   passage change valve means, comprising a single valve member connected to said supply means, said furnace, said oxidizing means, said first and second gas-chromatographic columns and said first thermal conductivity detecting means, said single valve member being movable between first and second positions, for, when said single valve member is in said first position, connecting said supply means to said furnace, connecting said oxidizing means to a first end of said first gas-chromatographic column, and connecting said first gas-chromatographic column to said second gas-chromatographic column, such that said carrier gas carries said gaseous mixture to said oxidizing means, carries said mixture in a first direction to said first gas-chromatographic column whereat said N$_2$ and CO$_2$ are separated from said H$_2$O which is retained therein, and carries said N$_2$ and CO$_2$ to said second gas-chromatographic column whereat said N$_2$ is separated from said CO$_2$, and for, when said single valve member is in said second position, connecting said supply means to a second end of said first gas-chromatographic column, connecting said first gas-chromatographic column to said first thermal conductivity detecting means, and connecting said supply means to said second gas-chromatograhic column, such that said carrier gas carries said H$_2$O retained in said first gas-chromatographic column in a second direction opposite to said first direction to said first thermal conductivity detecting means, thereby flushing said H$_2$O from said first gas-chromatographic column and detecting the quantity of the thus flushed H$_2$O, and such that said carrier gas carries said N$_2$ and CO$_2$ through said second gas-chromatographic column and then sequentially carries said N$_2$ and CO$_2$ to said second thermal conductivity detecting means for detecting the relative quantities thereof.

2. An apparatus for analyzing respective quantities of ozygen, nitrogen and hydrogen contained in metals, said apparatus comprising:
   a graphite crucible for receiving a metal sample therein;
   a heating furnace operatively associated with said crucible for heating said crucible and sample thereby generating a gaseous mixture of CO, N$_2$ and H$_2$;
   supply means for supplying a carrier gas for carrying away said gaseous mixture of CO, N$_2$ and H$_2$;
   oxidizing means connected to said heating furnace for receiving said gaseous mixture and oxidizing said gaseous mixture into a mixture H$_2$O, CO$_2$ and N$_2$;
   a first gas-chromatographic column for separating the H$_2$O from said mixture;
   a second gas-chromatographic column for separating the N$_2$ from the CO$_2$;
   a single thermal conductivity detecting means connected to said second gas-chromatographic column for detecting quantitities of CO$_2$, N$_2$ and H$_2$O generated from said sample; and
   passage change valve means, comprising a single valve member connected to said supply means, said furnace, said oxidizing means, said first and second gas-chromatographic columns and said thermal conductivity detecting means, said single valve member being movable between first and second positions, for, when said single valve member is in said first position, connecting said supply means to said furnace, connecting said oxidizing means to a first end of said first gas-chromatographic column, and connecting said first gas-chromatograhic column to said second gas-chromatographic column, such that said carrier gas carries said gaseous mixture to said oxidizing means, carries said mixture in a first direction to said first gas-chromatographic column whereat said N$_2$ and CO$_2$ are separated from said H$_2$O which is retained therein, carries said N$_2$ and CO$_2$ to said second gas-chromatographic column whereat said N$_2$ is separated from said CO$_2$, and sequentially carries said N$_2$ and CO$_2$ to said thermal conductivity detecting means for detecting the relative quantities thereof, and for, when said single valve member is in said second position, connecting said supply means to a second end of said first gas-chromatographic column, and connecting said first gas-chromatographic column to said thermal conductivity detecting means, such that said carrier gas carries said H$_2$O retained in said first gas-chromatographic column in a second direction opposite to said first direction to said thermal conductivity detecting means, thereby flushing said H$_2$O from said first gas-chromatographic column and detecting the quantity of the thus flushed H$_2$O.

3. An apparatus as claimed in claims 1 or 2, wherein said first gas-chromatographic column has a filler therein for causing the elution time for H$_2$O to be greater than the elution time for CO$_2$ and N$_2$.

4. An apparatus as claimed in claims 1 or 2, wherein said supply means comprises a carrier gas supply route extending through said single valve member for supplying said carrier gas therethrough, and a purging channel extending through said single valve member to said heating furnace for supplying said carrier gas for purging said system when said single valve member is in said second position.

5. An apparatus as claimed in claim 1, further comprising delay means connected between said single valve member and said second gas-chromatographic column for delaying passage of said $N_2$ and $CO_2$ through said second gas-chromatographic column to said thermal conductivity detecting means by a sufficient amount of time for allowing said $H_2O$ to pass from said first gas-chromatographic column to said thermal conductivity detecting means.

* * * * *